US008909613B2

(12) United States Patent
Treu et al.

(10) Patent No.: US 8,909,613 B2
(45) Date of Patent: Dec. 9, 2014

(54) SYSTEM AND METHOD FOR IDENTIFYING AND PAIRING DEVICES

(75) Inventors: Dennis M. Treu, Bedford, NH (US); Kevin Albiston, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 269 days.

(21) Appl. No.: 13/467,553

(22) Filed: May 9, 2012

(65) Prior Publication Data

US 2012/0221634 A1 Aug. 30, 2012

Related U.S. Application Data

(63) Continuation of application No. 12/815,030, filed on Jun. 14, 2010, now Pat. No. 8,190,651.

(60) Provisional application No. 61/187,227, filed on Jun. 15, 2009.

(51) Int. Cl.
*G06F 7/00* (2006.01)
*G06F 19/00* (2011.01)

(52) U.S. Cl.
CPC ........ *G06F 19/3418* (2013.01); *G06F 19/3412* (2013.01); *Y10S 707/959* (2013.01); *Y10S 707/967* (2013.01)
USPC ........... 707/705; 707/959; 707/967; 709/227; 709/237

(58) Field of Classification Search
CPC .................................................. G06F 19/3412
USPC ................... 707/705, 959, 967; 709/227, 237
See application file for complete search history.

(56) References Cited

U.S. PATENT DOCUMENTS

| 5,178,627 | A | | 1/1993 | Hudock |
| 5,549,117 | A | * | 8/1996 | Tacklind et al. ............. 600/529 |
| 5,598,536 | A | | 1/1997 | Slaughter, III et al. |
| 5,623,242 | A | | 4/1997 | Dawson, Jr. et al. |
| 5,950,632 | A | | 9/1999 | Reber et al. |
| 5,974,124 | A | | 10/1999 | Schlueter, Jr. et al. |
| 6,024,699 | A | | 2/2000 | Surwit et al. |
| 6,122,351 | A | * | 9/2000 | Schlueter et al. ......... 379/106.02 |
| 6,154,843 | A | | 11/2000 | Hart, Jr. et al. |
| 6,203,495 | B1 | * | 3/2001 | Bardy .......................... 600/301 |
| 6,304,881 | B1 | | 10/2001 | Halim et al. |
| 6,313,853 | B1 | | 11/2001 | Lamontagne et al. |
| 6,442,432 | B2 | | 8/2002 | Lee |

(Continued)

FOREIGN PATENT DOCUMENTS

EP 0911065 A2 4/1999

*Primary Examiner* — Cheyne D Ly
(74) *Attorney, Agent, or Firm* — Miles & Stockbridge, P.C.; Mark A. Catan

(57) ABSTRACT

A computer system and method for identifying and pairing devices. The system includes a plurality of remote user interface computers, each having a display device and a user input device and each connected to a first network via a first respective data communication link. The system also includes a plurality of medical devices each having a medical device user interface and a second data communication link adapted to exchange data with the remote user interface computers. The system also includes a database adapted to communicate with the remote user interface computers via a connection to the first network or via a direct connection to one of the remote user interface computers, the database being adapted to store patient medical information including a treatment prescription that includes use of one of the medical devices.

22 Claims, 10 Drawing Sheets

(56) References Cited

U.S. PATENT DOCUMENTS

| | | |
|---|---|---|
| 6,551,243 B2 | 4/2003 | Bocionek et al. |
| 6,589,169 B1 | 7/2003 | Surwit et al. |
| 6,598,084 B1 | 7/2003 | Edwards et al. |
| 6,681,003 B2 * | 1/2004 | Linder et al. ............. 379/106.02 |
| 6,738,671 B2 | 5/2004 | Christophersom et al. |
| 6,747,556 B2 | 6/2004 | Medema et al. |
| 6,807,543 B2 | 10/2004 | Muthya |
| 6,850,889 B1 | 2/2005 | Zayas, Jr. |
| 6,874,085 B1 | 3/2005 | Koo et al. |
| 6,937,150 B2 | 8/2005 | Medema et al. |
| 6,988,075 B1 * | 1/2006 | Hacker ............................. 705/3 |
| 6,988,088 B1 | 1/2006 | Miikkulainen et al. |
| 7,003,260 B1 | 2/2006 | Kessler et al. |
| 7,103,578 B2 | 9/2006 | Beck et al. |
| 7,258,665 B2 | 8/2007 | Kohls et al. |
| 7,260,402 B1 | 8/2007 | Ahmed |
| 7,337,129 B1 | 2/2008 | Lowry et al. |
| 7,349,907 B2 | 3/2008 | Celik |
| 7,353,179 B2 | 4/2008 | Ott et al. |
| 7,383,088 B2 | 6/2008 | Spinelli et al. |
| 7,386,462 B2 | 6/2008 | Silva-Craig et al. |
| 7,426,475 B1 | 9/2008 | Tangellapally et al. |
| 7,438,228 B2 | 10/2008 | Robertson et al. |
| 7,447,643 B1 | 11/2008 | Olson et al. |
| 7,457,804 B2 | 11/2008 | Uber, III et al. |
| 7,464,042 B2 | 12/2008 | Beraja et al. |
| 7,490,046 B1 | 2/2009 | Wyatt |
| 7,505,867 B2 | 3/2009 | Bharara et al. |
| 7,539,665 B2 | 5/2009 | Mendez |
| 7,542,911 B2 | 6/2009 | Barret et al. |
| 7,668,736 B2 | 2/2010 | Jones et al. |
| 7,698,156 B2 | 4/2010 | Martucci et al. |
| 7,752,058 B2 | 7/2010 | Sasaki et al. |
| 7,761,311 B2 | 7/2010 | Clements et al. |
| 7,779,183 B2 | 8/2010 | Koehler et al. |
| 7,860,725 B2 | 12/2010 | Gopinathan et al. |
| 7,870,006 B2 | 1/2011 | Tkaczyk et al. |
| 7,899,683 B2 | 3/2011 | Schoenberg et al. |
| 7,899,910 B1 | 3/2011 | Mosleh et al. |
| 7,908,151 B2 | 3/2011 | Heckerman et al. |
| 7,908,154 B2 | 3/2011 | Kalamas |
| 7,912,733 B2 | 3/2011 | Clements et al. |
| 7,917,628 B2 * | 3/2011 | Hesselink et al. ............ 709/227 |
| 2002/0156864 A1 * | 10/2002 | Kniest .......................... 709/217 |
| 2005/0119941 A1 | 6/2005 | James |
| 2005/0171411 A1 * | 8/2005 | KenKnight et al. ........... 600/300 |
| 2007/0100697 A1 | 5/2007 | Kolla |
| 2008/0285626 A1 * | 11/2008 | Claus et al. ................... 375/133 |
| 2009/0231124 A1 * | 9/2009 | Klabunde et al. ........ 340/539.12 |
| 2009/0260064 A1 | 10/2009 | McDowell et al. |
| 2009/0276515 A1 * | 11/2009 | Thomas et al. ............... 709/223 |
| 2010/0115279 A1 * | 5/2010 | Frikart et al. ................. 713/171 |

* cited by examiner

SYSTEM AND METHOD FOR IDENTIFYING AND PAIRING DEVICES

CROSS-REFERENCE TO RELATED APPLICATIONS

This application is a continuation of U.S. application Ser. No. 12/815,030 filed Jun. 14, 2010, which claims the benefit of U.S. Provisional Application No. 61/187,227, entitled "System and Method for Identifying and Pairing Devices" filed Jun. 15, 2009, both of which being incorporated herein by reference in their entireties.

Embodiments generally relate to identification and pairing of electronic devices, and, more particularly, to identification and pairing of wireless medical devices within a multi-patient, multi-device environment.

There are environments and settings in which devices must be identified and paired correctly in order to perform a task properly or safely. In some of these environments, such as a medical or health care delivery setting, correct identification and pairing of devices may be critical. However, it may not be desirable for the paired devices to be electrically coupled to one another due to safety requirements surrounding the design, testing and approval of medical devices. Accordingly, it may be advantageous to permit the devices to be identified and paired via a wireless connection.

Embodiments were conceived in light of the above considerations, among other things. For example, a system and method for identifying and pairing devices in accordance with this disclosure can provide an ability to identify a user via a remote user interface computer, and identify one or more medical devices to be paired with the remote user interface computer for administering treatment to a patient or sensing a physical parameter (or vital statistic) of the patient.

One embodiment includes a system for device identification and pairing. The system includes a plurality of remote user interface computers, each including a display device and a user input device and each connected to a first network via a first respective data communication link; and a plurality of medical devices each having a medical device user interface and a second data communication link adapted to exchange data with the remote user interface computers.

The system can also include a database (or data store) adapted to store patient medical information including a treatment prescription that includes use of one of the medical devices. The database can be a database server adapted to communicate with the remote user interface computers via a connection to the first network. The database can also be a computer readable medium (e.g., a USB flash drive) designed to directly connect to the remote user interface computer and having the patient medical information stored thereon. Each remote user interface computer can be associated with a patient based on identification and verification information entered by an operator to the remote user interface computer via the user input device. And, depending on the patient identification and verification, the remote user interface computer retrieves the treatment prescription associated with the patient from the server or computer readable medium. Also, based on the treatment prescription, the remote user interface computer senses, using the second data communication link, the available devices indicated for use in the treatment prescription, and prompts the operator to enter a verification key sequence generated by the remote user interface computer on a selected device that the operator intends to use for treating the patient. And, when the remote user interface computer does not receive a verification key sequence or receives an incorrect key sequence from one or more of the medical devices, the operator is prompted to retry the key sequence or change devices.

When the remote user interface computer receives a correct verification key sequence from the selected medical device, the remote user interface computer identifies the selected medical device as the one the operator intends to use and pairs with the selected medical device to establish a communication link for carrying out the prescribed treatment.

Another embodiment includes a method for identifying a medical device and pairing the identified medical device with a remote user interface computer. The method includes receiving patient identification information representing the identity of a patient; and verifying the patient identification information using information stored in a server accessible via a first network. The method also includes receiving, based on verified patient identification information, a prescribed medical treatment regimen from the server, and scanning for medical devices connected to a second network.

If devices needed for carrying out the prescribed medical treatment regimen are present and connected, patient identification and connected devices are displayed. The method includes determining if a multi-system environment is present, and if a multi-system environment is present, carrying out a first operational sequence.

The first operational sequence includes displaying patient identification and devices to verify, and for each device to verify, receiving input from an operator indicating a selected device to verify. The first operational sequence also includes displaying patient identification and a verification key sequence, and receiving key sequence data from the selected device. The first operational sequence further includes verifying the received key sequence data, and indicating that the selected device is verified when the received key sequence data matches the displayed verification key sequence. The first operational sequence also includes displaying selected device and prompting the operator to retry or change devices when the received key sequence data does not match the displayed verification key sequence, and repeating the first operational sequence until all devices are verified.

If a multi-system environment is not present or if all devices in the multi-system environment have been verified, then a second operational sequence is carried out. The second operational sequence includes displaying patient identification and verified devices, and exchanging handshake signals with each verified device, respectively. The second operational sequence also includes initiating the prescribed medical treatment regimen.

DETAILED DESCRIPTION

Figure 1:
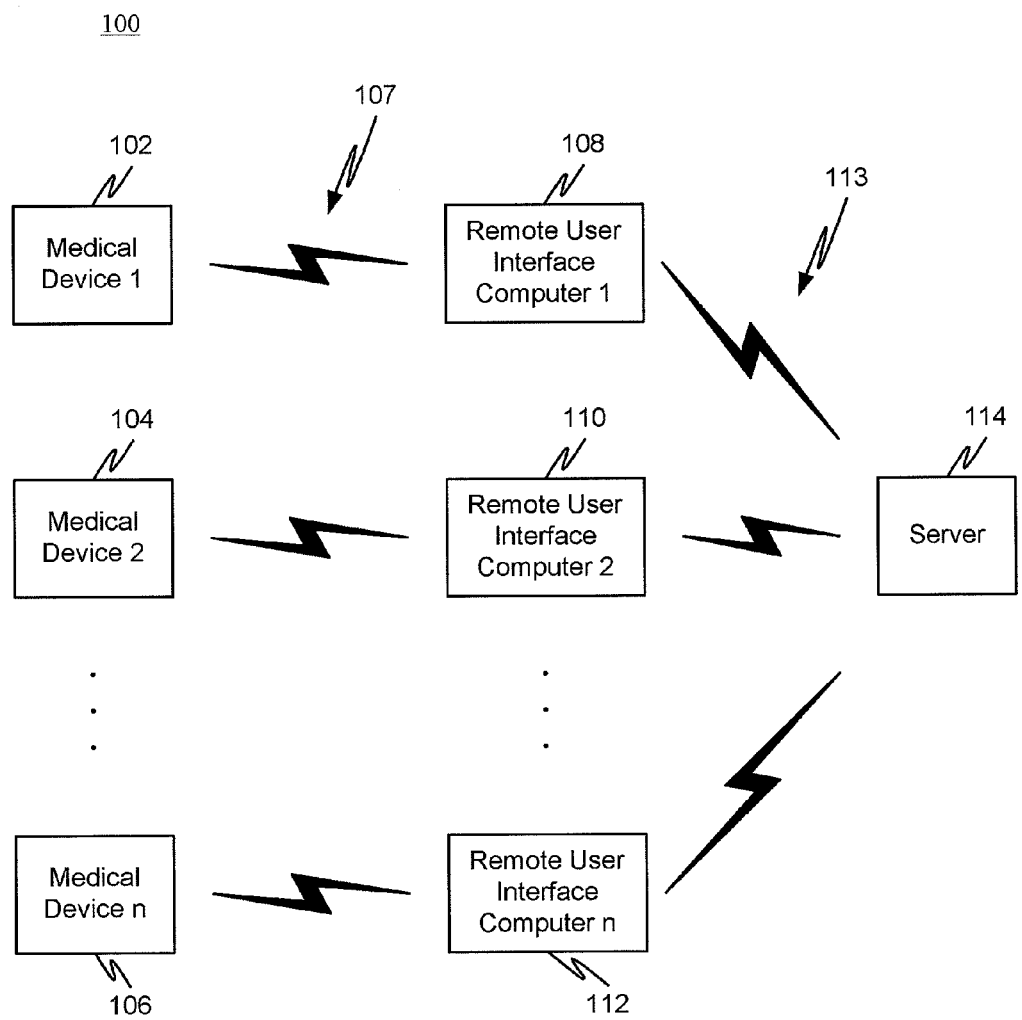
FIG. 1 is a diagram of a system for identifying and pairing devices in accordance with an embodiment for use in an exemplary multi-system environment.

FIG. 1 is a diagram of a system for identifying and pairing devices in accordance with an embodiment for use in an exemplary multi-system environment. In particular, FIG. 1 shows an exemplary system 100 including a plurality of medical devices (102-106), a plurality of remote user interface computers (108-112) and a server computer system 114. The medical devices (102-106) communicate with the remote user interface computers (108-112) via links 107. The remote user interface computers (108-112) communicate with the server 114 via links 113. The links (107 and 113) can be wired or wireless connections. The medical devices (102-106) can include dialysis machines, blood pressure monitors, thermometers, heart monitors, blood oxygen monitors, weight scales, or the like. The medical devices (102-106) can be of the same or different type.

In operation, a patient or health care provider can select one of the remote user interface computers (108-112) to access a medical treatment or monitoring regimen for the patient. In connection with the medical treatment or monitoring regimen, the selected remote user interface computer (one of 108-112) can identify available medical devices (102-106) and establish a connection with a selected medical device. When administering medical treatment or monitoring regimens it is important that medical devices be correctly correlated with the patients such that the proper treatment or monitoring function is carried out. In order to determine which medical device has been selected for use with a particular patient, the remote user interface computer can perform a verification sequence to pair a selected medical device with the remote user interface computer being used for the patient.

In other words, the patient, medical treatment or monitoring regimen, remote user interface computer and medical device(s) must all be known, verified, and correctly correlated with each other in order to help ensure proper delivery of health care services. The patient can be identified and have their identity verified through a login process in which the patient (or health care provider or other operator) enters an identification value (e.g., name, identification umber, or the like) and a password on one of the remote user interface computers (108-112). Once the patient identity is verified, the medical treatment or monitoring regimen for that patient can be retrieved from the server 114. Once the treatment or monitoring regimen has been retrieved from the server 114 by the remote user interface computer (108-112) the patient has logged into, the remote user interface computer can determine if the needed medical devices (102-106) are already connected to the remote user interface computer or are available for connection. Once the medical devices needed for the treatment or monitoring are determined, the patient (or health care provider or other operator) can confirm that the remote user interface computer is properly paired with each device by performing an authentication sequence for each medical device being used for the patient. Through this procedure, described below in greater detail, each element of treatment or monitoring can be verified and properly correlated with the patient and medical devices being used for the patient. This process can be particularly important in multi-patient, multi-system environments.

Figure 2:
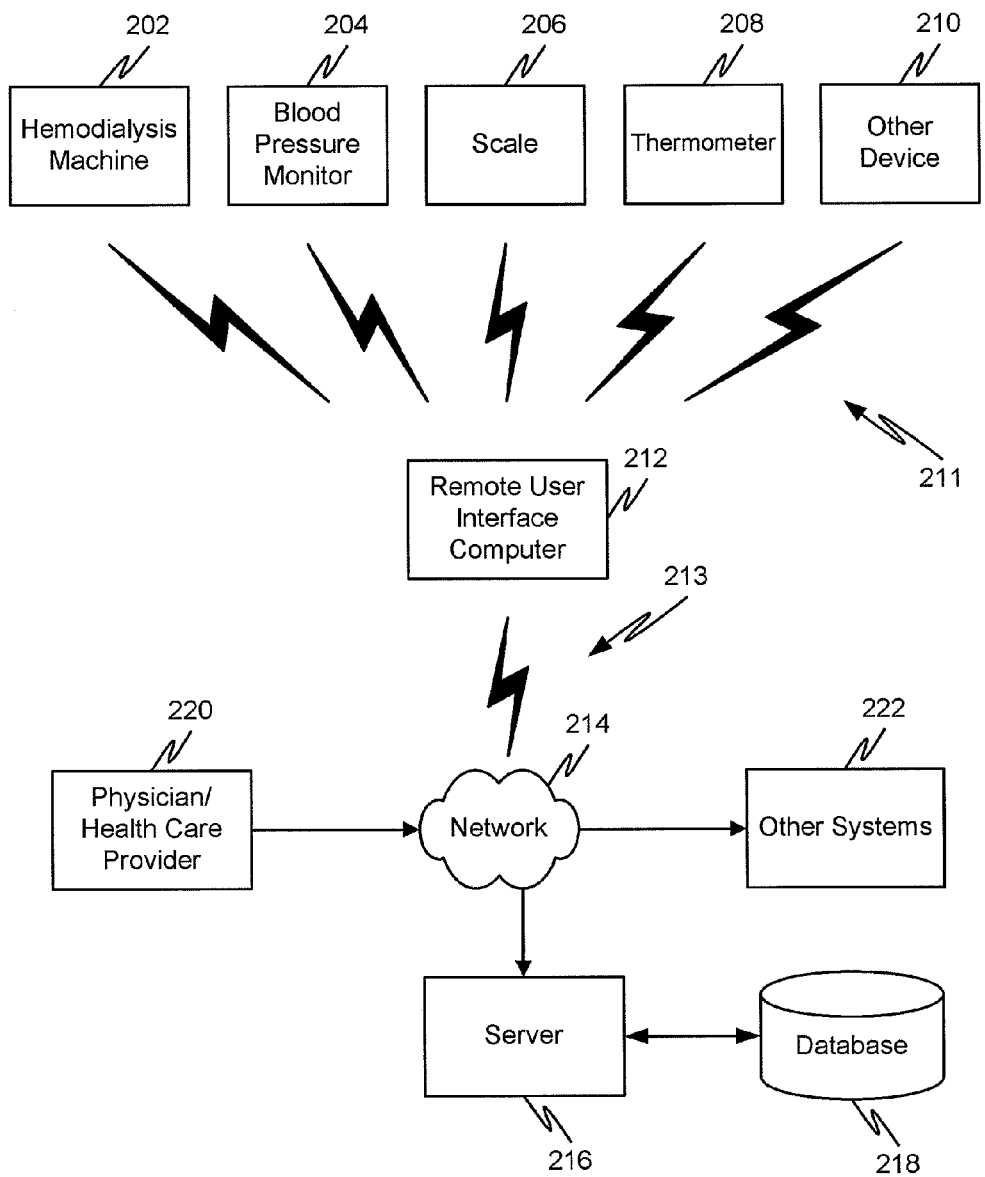
FIG. 2 is a diagram of a system for identifying and pairing devices in accordance with an embodiment and showing an exemplary configuration including multiple devices.

FIG. 2 is a diagram of a system for identifying and pairing devices in accordance with an embodiment showing an exemplary configuration including multiple medical devices. In particular, a system 200 includes a plurality of medical devices (202-210), a remote user interface computer 212, a network 214, a server 216 coupled to a database 218, a physician (or other health care provider) system 220 and other system(s) 222. The medical devices include a hemodialysis machine 202 (e.g., a cycler), a blood pressure monitor 204, a weight scale 206, a thermometer 208, and other devices 210.

The medical devices (202-210) are coupled to the remote user interface computer 212 via links 211. The remote user interface computer 212 is coupled to the network 214 via link 213. The links 211 and 213 can be wired or wireless links. The network 214 can be a local area network (LAN), wide area network (WAN), virtual private network (VPN), private network, public network, the Internet, or the like.

The remote user interface computer 212 can identify and pair with the medical devices (202-210) in order to exchange data with the medical devices (202-210). In addition to communicating with the medical devices (202-210), the remote user interface computer 212 can communicate with the server 216, the physician system 220, and other systems 222. By communicating with the server 216 the remote user interface computer 212 can exchange patient identification and medical information, such as prescribed treatment or monitoring regimens and data obtained during treatment or monitoring sessions. The server 216 can store patient identification and medical data in the database 218. Also, the server 216 can store medical device information and other information in the database 218.

The remote user interface computer 212 can communicate with the physician system 220 to permit a physician or health care provider to change a prescribed treatment or monitoring regimen, add or remove prescribed regimens, and monitor a patient while the patient receives medical care. The changing and monitoring can occur in real time, as treatment or monitoring is being carried out.

Because the remote user interface computer 212 can be associated with a patient and the medical devices can be positively identified and paired with the remote user interface computer 212, health care providers can be more certain that a patient is receiving the correct treatment or monitoring.

The identification and pairing sequence, described in detail below, can be performed prior to beginning a treatment or monitoring session. The identification and pairing sequence can also be performed periodically during a session. For example, the identification and pairing procedure can be performed periodically in response to an automatically generated signal or in response to a manual request. For example, a patient or health care provider can request to verify the identification and pairing between a remote user interface computer and one or more of the medical devices. Also, the patient verification and device identification and pairing can be performed when a treatment or monitoring session stops or starts (e.g., each time a new patient is being treated, or when a patient needs to stop treatment temporarily and resume treatment later).

The other systems 222 coupled to the remote user interface computer 212 via the network 214 can include manufacturers, service providers, researchers, or the like. Data collected during treatment/monitoring sessions (e.g., log files, device diagnostic data, device prognostic data, and patient physiological data can be provided to a manufacturer in order to provide troubleshooting, maintenance, and training for health care providers or patients. The data can also be transmitted to services such as medical record data services, or to researchers. Data could also be sent to a monitoring service for monitoring home health care delivery to a patient.

Figure 3:
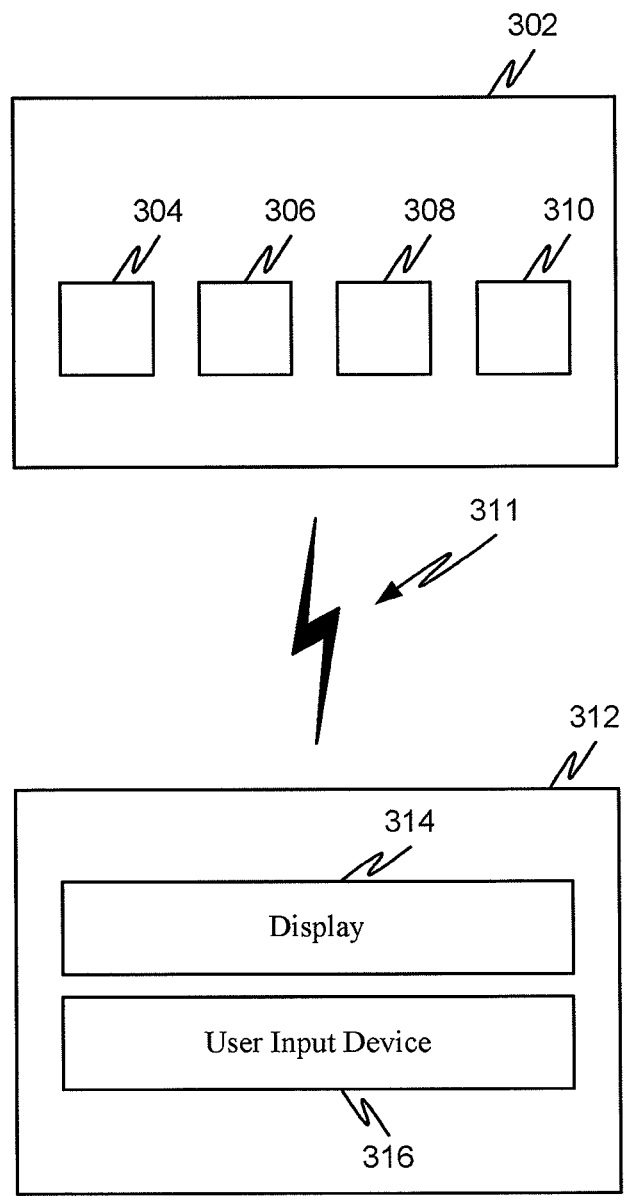
FIG. 3 is a diagram of a device and a remote user interface computer in accordance with an embodiment having exemplary user interface elements.

FIG. 3 is a diagram of a device and a remote user interface computer in accordance with an embodiment showing exemplary user interface elements. In particular, a system 300 includes a medical device 302 and a remote user interface computer 312. The remote user interface computer 312 can communicate with the medical device 302 via a link 311. The link 311 can be a wireless link (e.g., Wi-Fi, Bluetooth, or cell modem) or a wired link. The medical device 302 includes a plurality of buttons (304-310). The remote user interface computer 312 includes a display device 314 and a user input device 316.

Examples of display devices include cathode ray tubes (CRTs), liquid crystal displays (LCDs), plasma displays, light emitting diode (LED) displays, and the like. The user input device can include one or more of a keyboard, mouse, trackball, touchpad, touchscreen, keypad, switch, button, dial, knob, or the like.

In operation, a patient or operator can enter patient identification and password information on the user input device 316 of the remote user interface computer 312. The patient identification information (e.g., name, ID number, or the like) can be displayed on the display device 314. Once the patient is logged in, the remote user interface computer 312 can detect and identify medical devices available for use and display information identifying those devices (e.g., device type, device number, or the like). Although the remote user interface computer 312 may be able to detect medical devices available for use, it may not be able to determine which device is intended for use with a particular patient. The pairing process, with its verification step, permits the remote user interface computer to associate a particular medical device with the patient logged in to the remote user interface computer 312.

The patient or operator can select a device to pair with on the remote user interface computer 312. The remote user interface computer 312 displays a verification key sequence on the display device 314. The verification key sequence can be a randomly generated sequence of keys for the user or patient to select (or press) on the medical device 302. The patient or operator then presses the keys (304-310) on the medical device 302 that correspond to the verification key sequence. For safety purposes the verification key sequence can be repeated, with a different verification key sequence, to ensure that the patient or user has positively identified and verified the medical intended to be used.

The medical device 302 then transmits the key sequence via link 311. The remote user interface computer 312 monitors link 311 for a communication from a medical device containing the verification key sequence. Along with transmitting the verification key sequence, the medical device may also transmit device identification information such as device identification number, network address, serial number, or the like. Once the remote user interface computer 312 receives a verification key sequence from a medical device 302 that matches the sequence displayed on the display device 314, the remote user interface computer 312 establishes a link with the medical device 302 and they are paired together for purposes of carrying out the medical treatment or monitoring.

Once paired, the remote user interface computer 312 and the medical device 302 exchange handshake messages to ensure that the devices remain connected correctly and the pairing remains intact. The handshake messages may be exchanged on a continuous, periodic, or on-demand basis. The handshake message may not contain data and may be sent periodically (e.g., every 5 seconds). The device may look for the handshake signal and determine that a remote user interface computer is no longer present if a handshake signal is not received within a predetermined interval (e.g., 15 seconds). Further, the remote user interface computer can communicate, via the handshake signal or otherwise, that the remote user interface computer has closed the link.

In addition to the handshake, another layer of security can be provided in which the system preserves pairing information during a power loss. For example, a device may not pair with a new remote user interface computer until a previous pairing is ended or broken. The previous pairing may be ended or broken in one of several ways including sending a message to the device or by physically pressing a reset button on the device (e.g., a button located in a hard to reach spot).

In addition to the verification key sequence process described above, an additional verification safety interlock could be used. The additional safety interlock includes the patient (or operator) entering an identification number read from the medical device 302 on the user input device 316 of the remote user interface terminal 312. When transmitting the verification key sequence, the medical device 302 could also transmit its identification number. The remote user interface computer 312 could then match the verification key sequence received from the medical device 302 with the verification key sequence displayed to the patient or operator, and match the medical device identification number entered into the user input device 316 of the remote user interface computer 312 with the medical device identification number received with the verification key sequence. In this way, a safety interlock mechanism could be implemented that includes a two-point verification process: matching both the verification key sequence and the medical device identification number. This safety interlock mechanism may be desirable in medical devices where patient safety is critical and a single point of failure may not be acceptable.

While a key sequence is described as a verification example for illustration purposes, other verification methods may be used as alternatives or in combination with a verification key sequence. Other verification methods include, but are not limited to, biometric, proximity detectors, RFID, identification cards and/or devices or the like. In general, any identification/verification technique or technology suitable for performing the authentication function described herein may be used.

Also, medical devices and remote user interface computers can include visual status indicators (such as lights or displays) to show their respective current operating states. For example, a green light could indicate an available state, a yellow light could indicate a pairing state and a red light could indicate a paired and transmitting state. This way, patients and health care providers can quickly assess device status and availability. Also, visual status indicators may reduce errors.

Because a pairing verification sequence can include a user pressing buttons or keys on a medical device, the medical devices can include a capability to protect patients from inadvertent changes to the device operation of a medical device in use. For example, when a remote user interface computer transmits a request to identify and/or pair with a medical device, this request can be received by devices that are in use. Then, when buttons or keys are pressed on a device that is in use, the device can prompt the user to confirm that a change in device operation is in fact desired and that this is not an erroneous attempt to enter a verification key sequence on a device that is currently in use. This checking and confirmation feature can be activated by receiving or sensing a request to identify and/or pair and can remain active for a predetermined period of time (e.g., five minutes).

The verification and pairing sequences described above can optionally be augmented with physical and/or visual identification and pairing. For example, medical devices and remote user interface terminals can be physically tethered using a communication cable (e.g., an Ethernet cable) in a multi-user environment. Such a tethering could provide a communication path in the event the wireless connection was not working, but would serve primarily as a physical tether. Also, medical device and remote user interface computers could each display an indication of pairing, such as displaying the same pairing number, patient name, color, symbol, or the like on each of the respective displays that are in a pairing.

Figure 4:
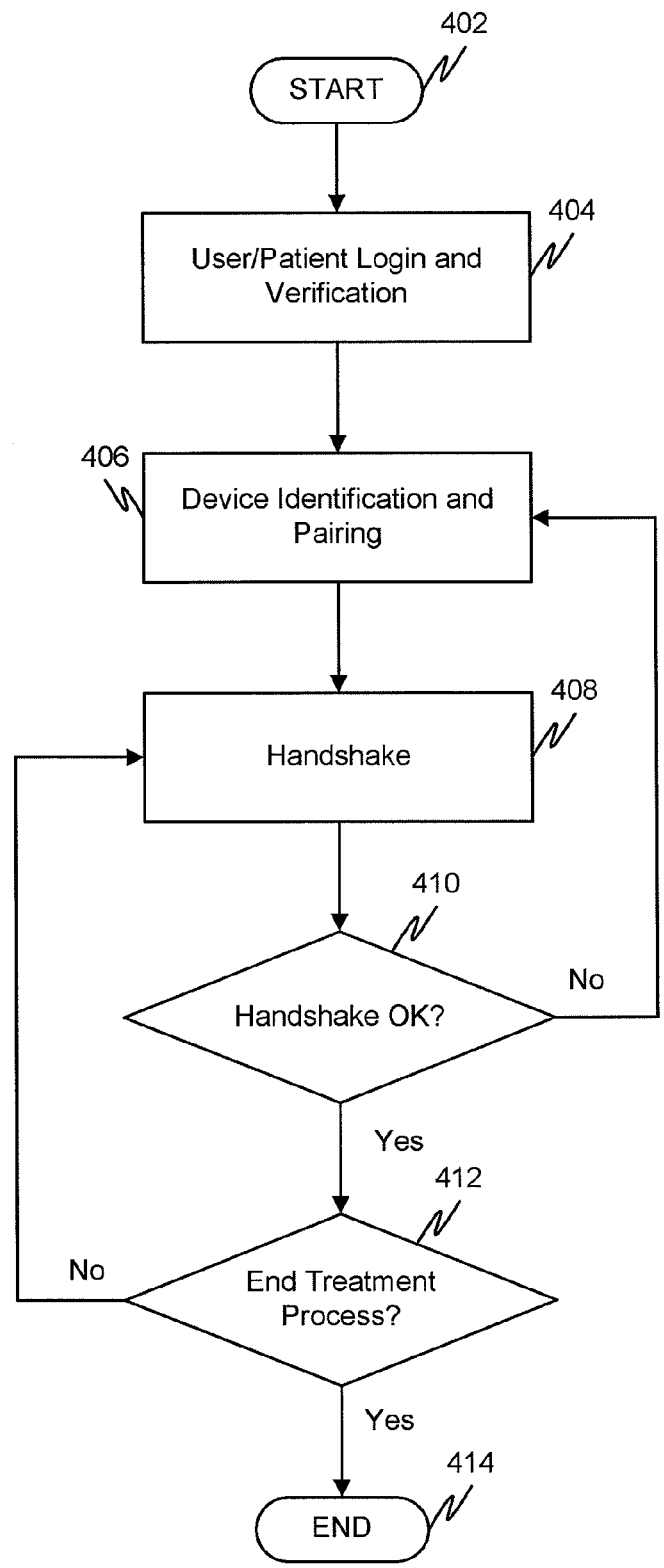
FIG. 4 is a high level diagram of a method for device identification and pairing in accordance with an embodiment.

FIG. 4 is a high level diagram of a method for device identification and pairing in accordance with an embodiment. In particular, processing begins at 402 and continues to 404.

At 404, a user (or patient) logs in and verifies identity on a remote user interface computer. Processing continues to 406.

At 406, a device identification and pairing process is performed, in which a remote user interface computer is paired with one or more medical devices. Processing continues to 408.

At 408, a handshake process (as described above) is performed. Processing continues to 410.

At 410, it is determined whether the handshake is valid. If the handshake is valid, processing continues to 412. Otherwise processing continues to 406.

At 412, it is determined whether the current medical treatment or monitoring regimen has ended. If the treatment/monitoring regimen has ended processing continues to 414, where processing ends. If the treatment/monitoring regimen has not ended, processing continues back to 408.

A method in accordance with the present disclosure can be embodied as software instructions stored on a nontransitory computer readable medium such as an electronic memory device (e.g., RAM, ROM, EEPROM, flash, or the like), an optical storage device (e.g., CD, DVD, or the like), a magnetic storage device (e.g., hard disk) or any nontransitory computer medium suitable for storing software instructions and/or data. A separate computer readable medium can be provided for each component of the system (e.g., medical device, remote user interface computer and database) and would have the software for that respective component stored thereon.

Figure 5:
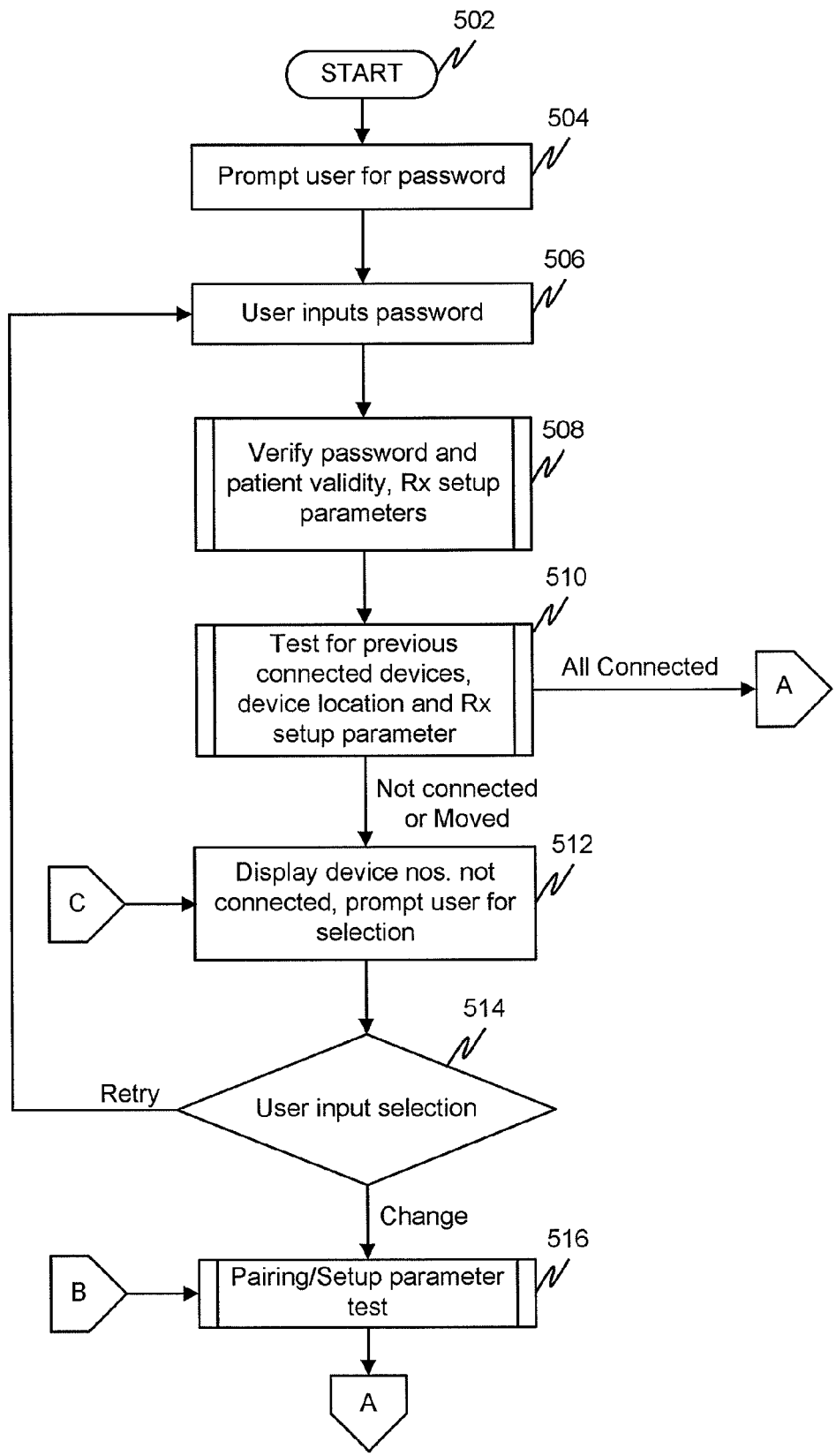
FIG. 5 is a diagram of an exemplary start-up phase of a method for device identification and pairing in accordance with an embodiment.

FIG. 5 is a diagram of an exemplary start-up phase of a method for device identification and pairing in accordance with an embodiment. In particular, processing begins at 502 and continues to 504.

At 504, the user (or patient) is prompted for a password. The user may also be prompted for a user identification. Processing continues to 506.

At 506, the user inputs their password (and optionally their user ID). Processing continues to 508.

At 508, the password is verified and the patient is determined to be valid. Set up parameters are received (such as prescribed treatment/monitoring regimen, or the like). Processing continues to 510.

At 510, a test is performed for previously connected devices, device locations, and received setup parameters. For previously connected devices, an abbreviated pairing/connection routine can be implemented and includes the following steps:
1) The remote user interface computer request a connection with the previously connected device;
2) The device agrees to the connection;
3) The device sends device data;
4) The remote user interface computer request current patient information; and
5) The device sends current patient information.

The setup parameter test can include determining if any patient specific parameter settings on the system have changed since the previous treatment (e.g., any devices or equipment replaced due to service swap, doctor's prescription changes due to office visit, etc.).

Figure 6:
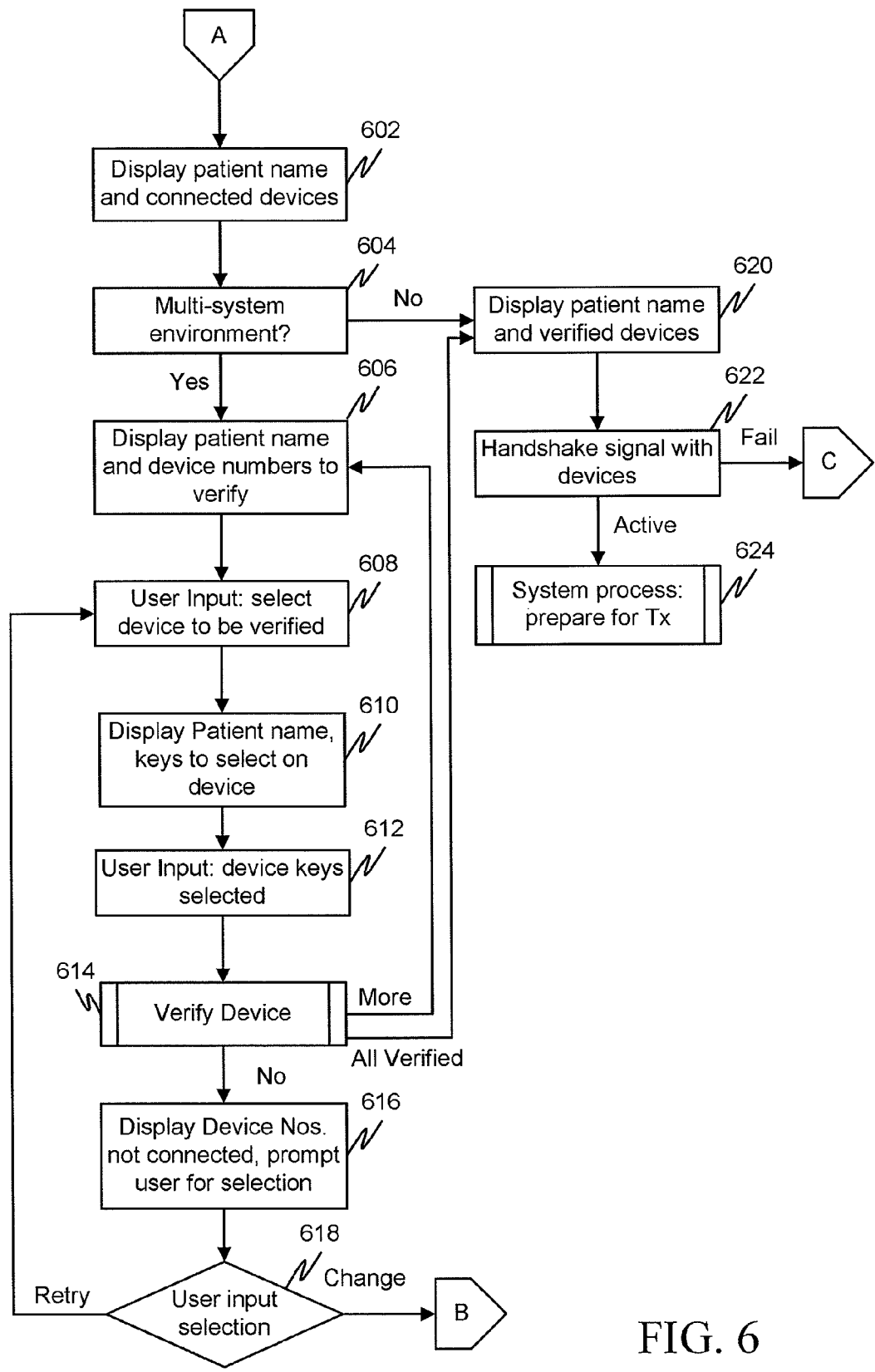
FIG. 6 is a continuation of the diagram in FIG. 5.

If all needed devices are connected, processing continues to 602 in FIG. 6 (see page connector "A"). If any needed device is not connected or has been moved, processing continues to 512.

At 512, device numbers of devices that are not connected are displayed. The user is prompted for a selection. Processing continues to 514.

At 514, the user selection evaluated. If the user selects to retry to connect to the devices, processing returns back to 506. If the user selects to change devices, processing continues to step 516.

At 516, a pairing and setup parameter test is performed. Pairing can include the following steps:
1) The remote user interface computer sends out a "Find" message;
2) All medical devices respond to the "Find" message with a response message;
3) The remote user interface computer may wait and repeat 1) to ensure that all devices have had an opportunity to respond;
4) The remote user interface computer requests a pairing with a particular device;
5) The device being requested for pairing agrees with pairing;
6) The remote user interface computer requests a connection to the device;
7) The device agrees to the connection;
8) The device send device data to the remote user interface computer;
9) The remote user interface computer requests patient information; and
10) The device sends patient information. The remote user interface computer and the device are now paired and connected. Processing continues to 602 in FIG. 6 (see off sheet connector "A").

FIG. 6 is a continuation of the diagram in FIG. 5. At 602, patient name and connected devices are displayed. Processing continues to 604.

At 604, it is determined whether a multi-system environment is present. If a multi-system environment is present processing continues to 606. Otherwise processing continues to 620.

At 606, patient name and device numbers to verify are displayed. Processing continues to 608.

At 608, user input indicating which device to verify is received. Processing continues to 610.

At 610, patient name and a verification key sequence are displayed. Processing continues to 612.

At 612, the patient (or operator) selects keys corresponding to the verification key sequence. Processing continues to 614.

At 614, the device is verified and it is determined whether any more devices need to be verified. If any selected devices were not able to be verified, processing continues to 616. If more devices need to be verified, processing continues to 606. If all devices are verified, processing continues to 620.

At 616, device numbers for devices not connected are displayed and the user is prompted for a selection between retry and changing. If the user selects to retry processing continues to 608. If the user prompts to change devices, processing continues 516 of FIG. 5 (see off sheet connector "B").

At 620, patient name and verified devices are displayed. Processing continues to 622.

At 622, an initial handshake signal is exchanged. If the handshake signal indicates that the medical devices are active, processing continues to 624. If the handshake signal indicates a failure with one or more devices, processing continues to 512 of FIG. 5 (see off sheet connector "C").

At 624, the system prepares for data transmission and exchange.

Figure 7:
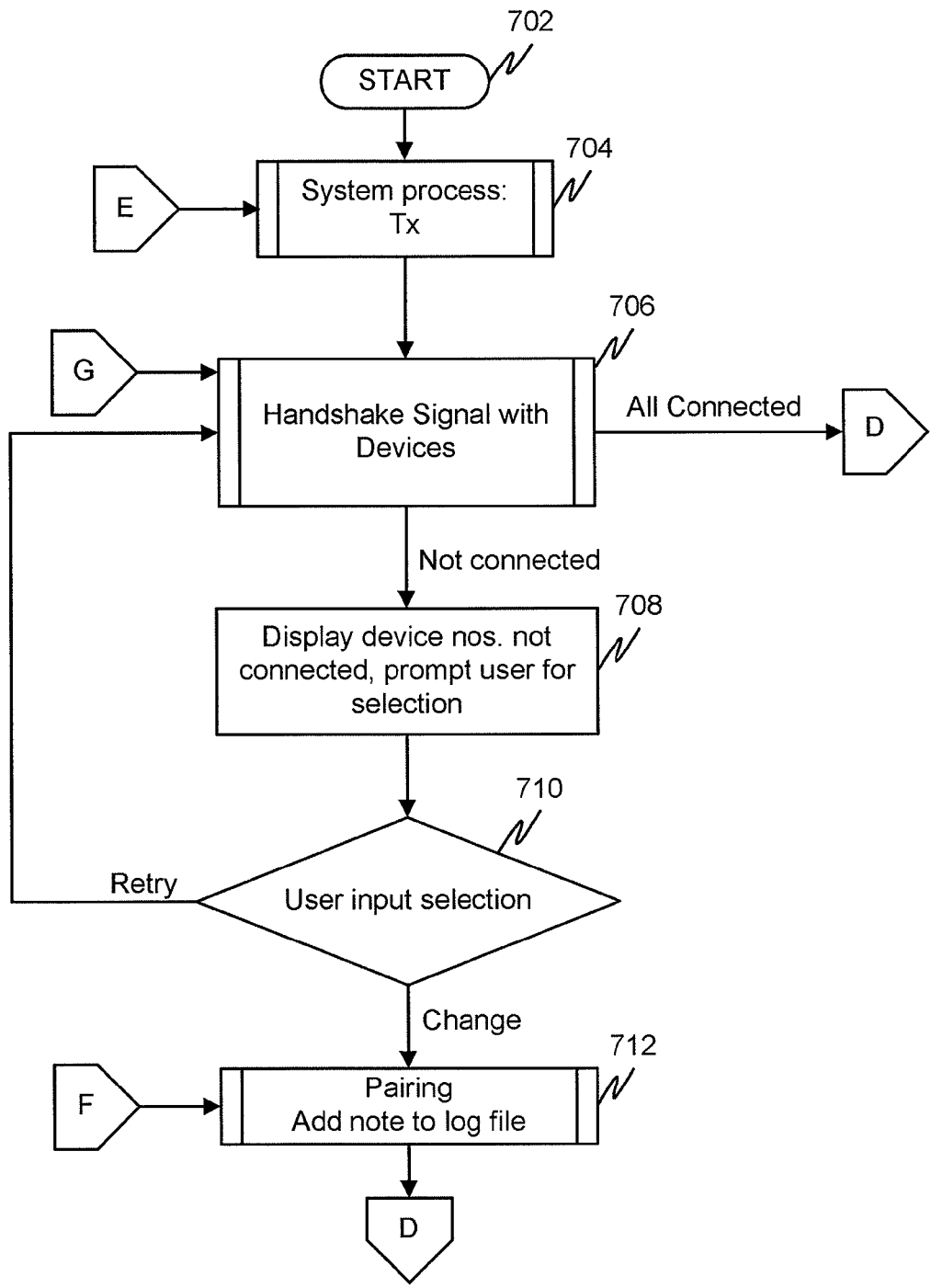
FIG. 7 is a diagram of an exemplary data transmit phase of a method for device identification and pairing in accordance with an embodiment.

FIG. 7 is a diagram of an exemplary data transmit phase of a method for device identification and pairing in accordance with an embodiment. In particular, processing starts at 702 and continues to 704.

At 704, the system transmit process begins. Processing continues to 706.

At 706, handshake signals are exchanged with devices. If the handshake signals indicate that all devices are connected, processing continues to 802 in FIG. 8 (see off sheet connector "D"). If one or more devices is not connected, processing continues to 708.

At 708, device numbers of devices not connected are displayed and the user is prompted for a selection between retrying and changing devices. Processing continues to 710.

At 710, the user input is evaluated. If the user selects to retry, processing continues back to 706. If the user selects to change devices, processing continues to 712.

At 712, the pairing process is performed and a note is added to a system log file. This assumes a non-cycler device was changed for some reason during treatment (e.g., service, etc.) and an indication of pairing the new device would be added to the log file. For example, the log file may be update with the model and serial number of the new device which could be automatically detected from the data stream produced by the newly-connected device, or could be manually entered during the pairing routine. Also, the verification step information could be logged. Processing continues to 802 of FIG. 8 (see off sheet connector "D").

Figure 8:
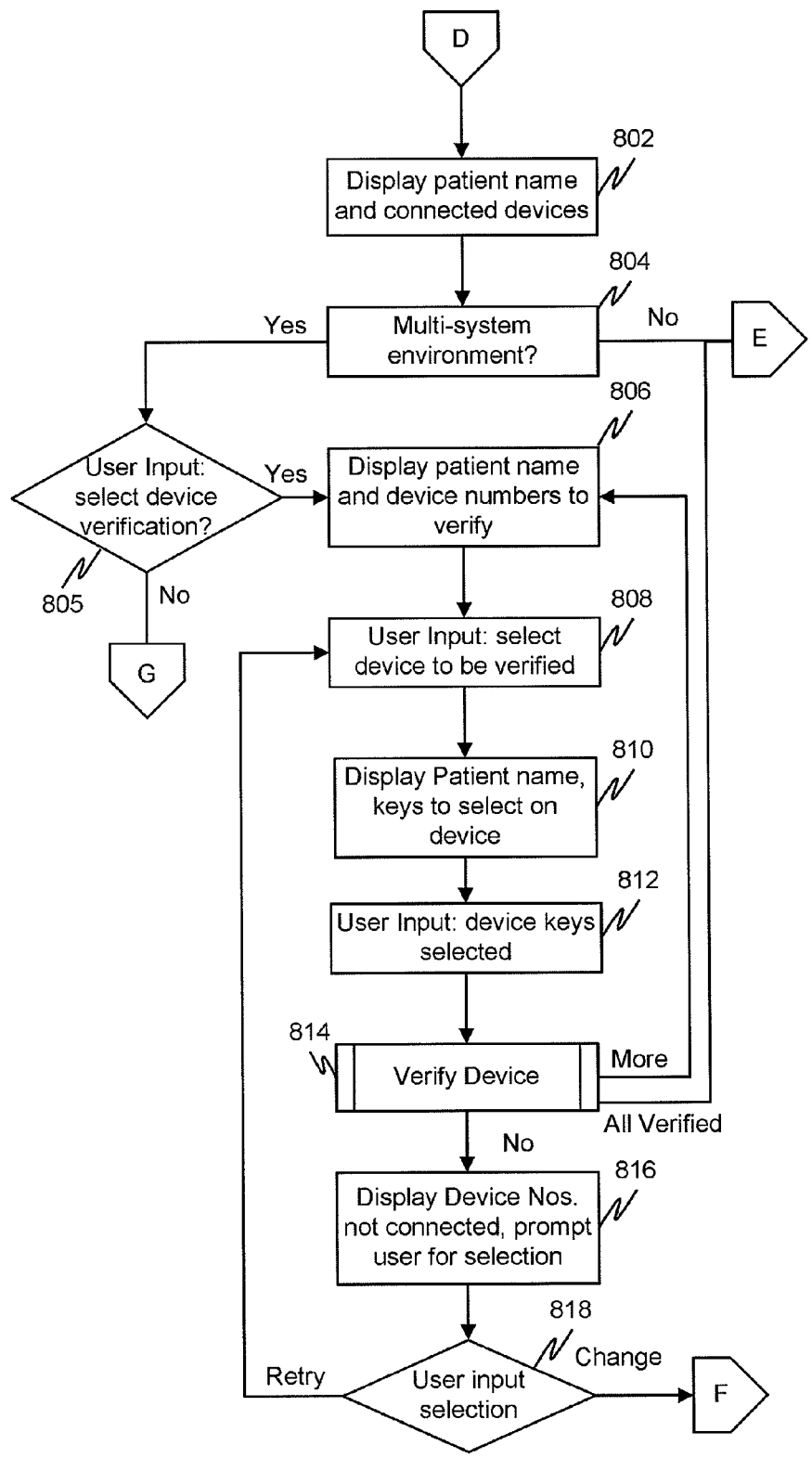
FIG. 8 is a continuation of the diagram in FIG. 7.

FIG. 8 is a continuation of the diagram in FIG. 7. Processing continues at 802, where patient name and connected devices are displayed. Processing continues to 804.

At 804, it is determined whether a multi-system environment is present. If a multi-system environment is present processing continues to 805. If a multi-system environment is not present, processing continues to 704 in FIG. 7 (see off sheet connector "E").

At 805, it is determined whether the user selects to perform device verification. If the user selects device verification processing continues to 806, otherwise processing returns to 706 in FIG. 7 (off sheet connector "G"). A user or operator may select to perform device verification in various situations, including when it becomes unclear which remote user interface computer or other device is being used for a particular patient (e.g., two remote user interface computers are set down on a table together). By requesting device verification, the user or operator can confirm the identification of the patient corresponding to the remote user interface computer or connected medical device.

At 806, patient name and device numbers to verify are displayed. In addition to reaching 806 from 804, 806 can be reached when a patient (or other user or operator) selects device verification 805. Processing continues to 808.

At 808, user input is received indicated a device selected to be verified. Processing continues to 810.

At 810, verification key sequence is displayed. Processing continues to 812.

At 812, user input indicating the verification key sequence is received. Processing continues to 814.

At 814, the device is verified and it is determined whether any more devices need to be verified. If any selected devices were not able to be verified, processing continues to 816. If more devices need to be verified, processing continues to 808. If all devices are verified, processing continues to 704 in FIG. 7 (see off sheet connector "E").

At 816, device numbers for devices not connected are displayed and the user is prompted for a selection between retry and changing. If the user selects to retry processing continues to 808. If the user prompts to change devices, processing continues 712 of FIG. 7 (see off sheet connecter "F").

Alternatively, as discussed above, 806-814 can be initiated by the user when the user selects device verification at 805.

Figure 9:
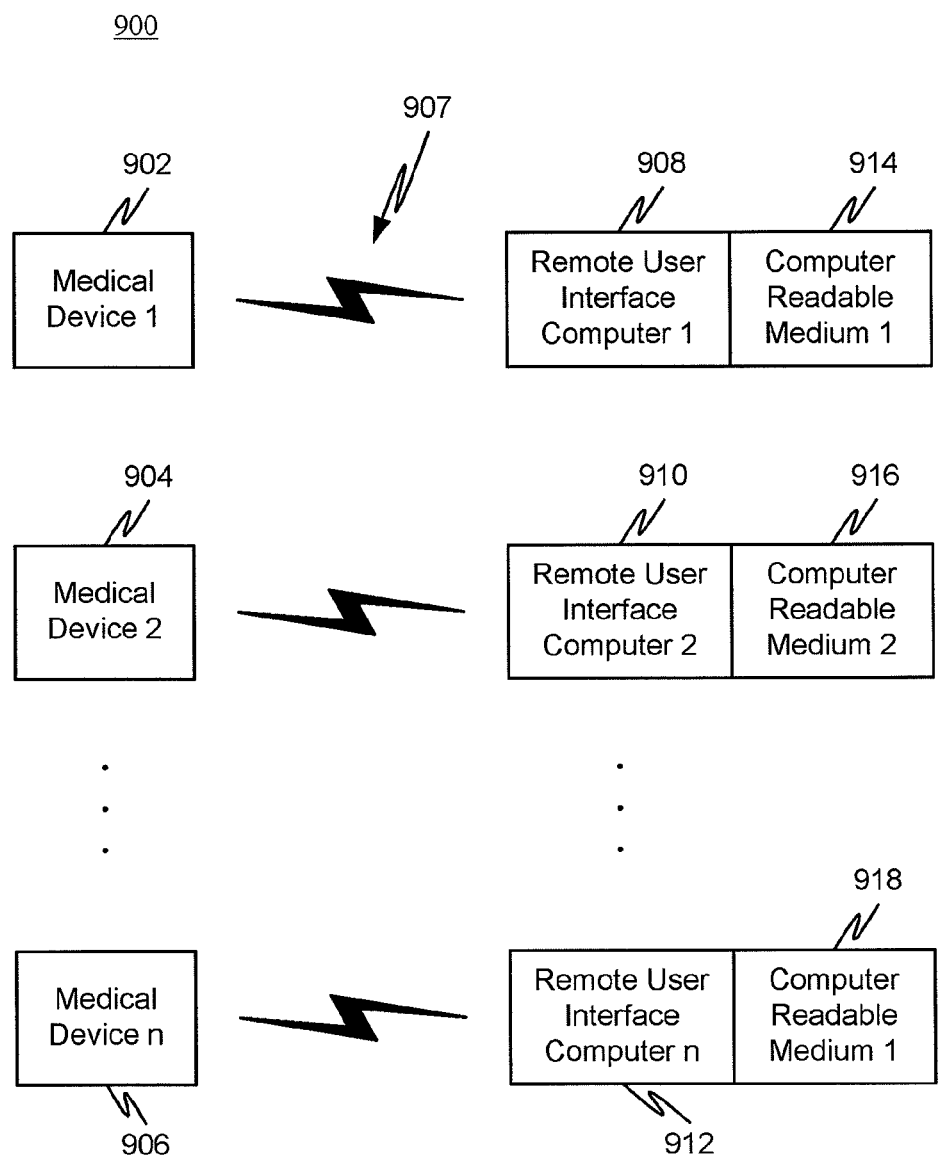
FIG. 9 is a diagram of a system for identifying and pairing devices in accordance with an embodiment for use in an exemplary multi-system environment and having a computer readable medium coupled to the remote user interface computer.

FIG. 9 is a diagram of a system for identifying and pairing devices in accordance with an embodiment for use in an exemplary multi-system environment and having a computer readable medium coupled to the remote user interface computer. In particular, FIG. 9 shows an exemplary system 900 including a plurality of medical devices (902-906), a plurality of remote user interface computers (908-912) each coupled to a respective computer readable medium (914-918). The medical devices (902-906) communicate with the remote user interface computers (908-912) via links 907. The remote user interface computers (908-912) are directly coupled to a respective computer readable medium (914-918) via a wired or wireless connection (e.g., via universal serial bus (USB) or the like). The links 907 can be wired or wireless connections. The medical devices (902-906) can include dialysis machines, blood pressure monitors, thermometers, heart monitors, blood oxygen monitors, weight scales, or the like. The medical devices (902-906) can be of the same or different type.

The computer readable media (914-918) can be, for example, a USB flash memory device or other portable computer readable medium adapted to be connected to a remote user interface computer such as an external hard disk or CD/DVD drive.

In operation, a patient or health care provider can select one of the remote user interface computers (908-912) to access a medical treatment or monitoring regimen for the patient. In connection with the medical treatment or monitoring regimen, the selected remote user interface computer (one of 908-912) can identify available medical devices (902-906) and establish a connection with a selected medical device. When administering medical treatment or monitoring regimens it is important that medical devices be correctly correlated with the patients such that the proper treatment or monitoring function is carried out. In order to determine which medical device has been selected for use with a particular patient, the remote user interface computer can perform a verification sequence to pair a selected medical device with the remote user interface computer being used for the patient.

In other words, the patient, medical treatment or monitoring regimen, remote user interface computer and medical device(s) must all be known, verified, and correctly correlated with each other in order to help ensure proper delivery of health care services. The patient can be identified and have their identity verified through a login process in which the patient (or health care provider or other operator) enters an identification value (e.g., name, identification umber, or the like) and a password on one of the remote user interface computers (908-912). The medical treatment or monitoring regimen for the patient can be retrieved from the corresponding computer readable medium (914-918). Once the treatment or monitoring regimen has been retrieved from the computer readable medium (914-918) connected to the remote user interface computer (908-912) the patient has logged into, the remote user interface computer can determine if the needed medical devices (902-906) are already connected to the remote user interface computer or are available for connection. Once the medical devices needed for the treatment or monitoring are determined, the patient (or health care provider or other operator) can confirm that the remote user interface computer is properly paired with each device by performing an authentication sequence for each medical device being used for the patient. Through this procedure, described below in greater detail, each element of treatment or monitoring can be verified and properly correlated with the patient and medical devices being used for the patient. This process can be particularly important in multi-patient, multi-system environments. Patient data can be retrieved from and/or stored to the respective computer readable medium (914-918).

Figure 10:
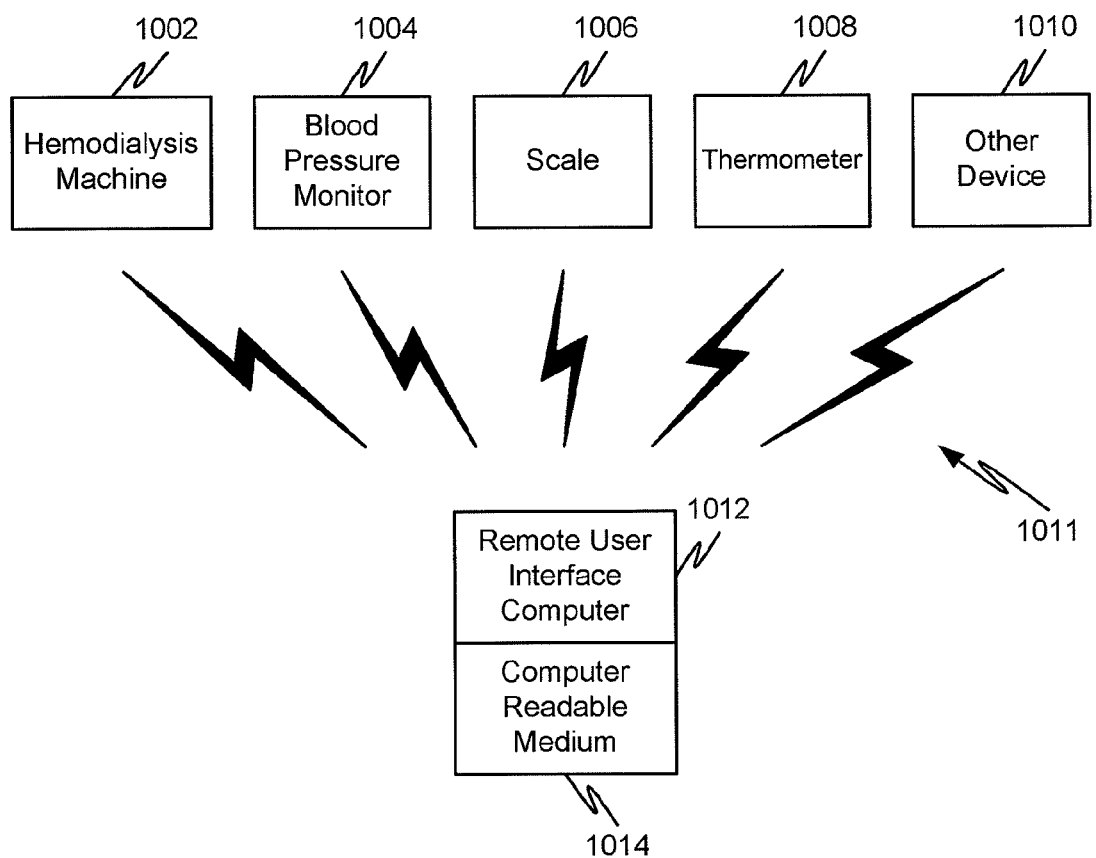
FIG. 10 is a diagram of a system for identifying and pairing devices in accordance with an embodiment and showing an exemplary configuration including multiple devices and a computer readable medium coupled to the remote user interface computer.

FIG. 10 is a diagram of a system for identifying and pairing devices in accordance with an embodiment and showing an exemplary configuration including multiple devices and a computer readable medium coupled to the remote user interface computer. In particular, a system 1000 includes a plurality of medical devices (1002-1010), a remote user interface computer 1012 and a computer readable medium 1014. The medical devices include a hemodialysis machine 1002 (e.g., a cycler), a blood pressure monitor 1004, a weight scale 1006, a thermometer 1008, and other devices 1010.

The medical devices (1002-1010) are coupled to the remote user interface computer 1012 via links 1011. The remote user interface computer 1012 is coupled to the computer readable medium 1014 via an interface such as USB or the like. The links 1011 and the interface between the remote user interface computer 1012 and the computer readable medium 1014 can be wired or wireless.

The remote user interface computer 1012 can identify and pair with the medical devices (1002-1010) in order to exchange data with the medical devices (1002-1010). In addition to communicating with the medical devices (1002-1010), the remote user interface computer 1012 can communicate with the computer readable medium 1014. By communicating with the computer readable medium 1014 the remote user interface computer 1012 can exchange patient identification and medical information, such as prescribed treatment or monitoring regimens and data obtained during treatment or monitoring sessions. The computer readable medium 1014 can store patient identification and medical data. Also, the computer readable medium 1014 can store medical device information and other information.

The identification and pairing sequence, described in detail above, can be performed prior to beginning a treatment or monitoring session. The identification and pairing sequence can also be performed periodically during a session. For example, the identification and pairing procedure can be performed periodically in response to an automatically generated signal or in response to a manual request. For example, a patient or health care provider can request to verify the identification and pairing between a remote user interface computer and one or more of the medical devices. Also, the patient verification and device identification and pairing can be performed when a treatment or monitoring session stops or starts (e.g., each time a new patient is being treated, or when a patient needs to stop treatment temporarily and resume treatment later).

Data collected during treatment/monitoring sessions (e.g., log files, device diagnostic data, device prognostic data, and patient physiological data can be stored to the computer readable medium 1014 and later provided to a manufacturer in order to provide troubleshooting, maintenance, and training for health care providers or patients. The data can also be transmitted to services such as medical record data services, or to researchers. Data could also be sent to a monitoring service for monitoring home health care delivery to a patient.

In addition to the exemplary embodiments shown above, an embodiment could include both a server (as shown in FIGS. 1 and 2) and a computer readable medium (as shown in FIGS. 9 and 10). The server and the computer readable medium could be used separately or together to provide patient data and/or store patient or device information.

Embodiments of the method and system for identifying and pairing devices, may be implemented on a general-purpose computer adapted for device identification and pairing, a special-purpose computer, a programmed microprocessor or microcontroller, a peripheral integrated circuit element, an ASIC or other integrated circuit, a digital signal processor, a hardwired electronic or logic circuit such as a discrete element circuit, a programmed logic device such as a PLD, PLA, FPGA, PAL, or the like. In general, any device or process capable of implementing the operations or steps described herein can be used to implement embodiments of the method and system for identifying and pairing devices.

Furthermore, a portion of embodiments of the disclosed method and system for identifying and pairing devices may be readily implemented in software using, for example, object or object-oriented software development environments that provide portable source code that can be used on a variety of computer platforms. Alternatively, embodiments of the disclosed method and system for identifying and pairing devices can be implemented partially or fully in hardware using, for example, standard logic circuits or a VLSI design. Other hardware or software can be used to implement embodiments depending on the speed and/or efficiency requirements of the systems, the particular function, and/or a particular software or hardware system, microprocessor, or microcomputer system being utilized. Embodiments of the method and system for identifying and pairing devices can be implemented in a hardware and software combination using any known or later developed systems or structures, devices and/or software by those of ordinary skill in the applicable art from the functional description provided herein and with a general basic knowledge of the computer and/or medical device arts.

Moreover, embodiments of the disclosed method and system for identifying and pairing devices can be implemented in part using software executed on a programmed general-purpose computer, a special purpose computer, a microprocessor, or the like. Also, the identifying and pairing devices method of this invention can be implemented in part as a program embedded on a personal computer such as a JAVA® or CGI script, as a resource residing on a server or graphics workstation, as a routine embedded in a dedicated processing system, or the like. The method and system can also be implemented by physically incorporating the method for identifying and pairing devices into a software and/or hardware system, such as systems for medical treatment or monitoring.

It is, therefore, apparent that there is provided in accordance with the present invention, a method and system for identifying and pairing devices. While this invention has been described in conjunction with a number of embodiments, it is evident that many alternatives, modifications and variations would be or are apparent to those of ordinary skill in the applicable arts. Accordingly, applicants intend to embrace all such alternatives, modifications, equivalents and variations that are within the spirit and scope of this invention.

What is claimed is:

1. A method for identifying a medical device and pairing the identified medical device with a remote user interface computer, the method comprising:
   receiving at the remote user interface identification information representing the identity of a patient;
   verifying the patient identification information using information stored in a database;
   receiving, based on verified patient identification information, a prescribed medical treatment regimen from the database;
   identifying a selected medical device available for carrying out the prescribed medical treatment;
   transmitting, using a data communication link, a pairing signal from the remote user interface computer to the identified medical device;
   receiving, using the data communication link, a pairing signal response from the identified medical device;
   comparing the pairing signal with the pairing signal response;
   establishing a communication link for carrying out the prescribed treatment based on a result of the comparison; and
   determining if a multi-system environment is present;
   if a multi-system environment is present, carrying out a first operational sequence including:
      displaying patient identification and devices to verify;
      for each device to verify:
         receiving input from an operator indicating a selected device to verify;
         displaying patient identification and a verification key sequence;
         receiving key sequence data from the selected device;
         verifying the received key sequence data;
         indicating that the selected device is verified when the received key sequence data matches the displayed verification key sequence;
         displaying a selected device and prompting the operator to retry or change devices when the received key sequence data does not match the displayed verification key sequence;
         repeating the first operational sequence until all devices are verified;
   if a multi-system environment is not present or if all devices in the multi-system environment have been verified, carrying out a second operational sequence including:
      displaying patient identification and verified devices;
      exchanging handshake signals with each verified device, respectively; and
      initiating the prescribed medical treatment regimen;
   when devices are not connected or moved, carrying out a third operational sequence comprising:
      displaying a list of available devices connected to a network and not connected to the remote user interface computer;
      prompting the operator to retry a connection with one or more devices or to change devices;
      receiving input data from the operator indicating whether the operator selected to retry or change devices;
      retrying to connect with one or more devices when the operator selects retry; and
      performing a pairing and setup parameter test when the operator selects to change devices.

2. The method of claim 1, wherein the pairing signal includes a signal prompting the operator to enter a sequence of keys on the identified medical device.

3. The method of claim 1, wherein the pairing response signal includes a sequence of keys actually entered by the operator on the identified medical device.

4. The method of claim 3, wherein when the prompted sequence of keys and the actual sequence of keys do not match, the communication link is not established.

5. The method of claim 1, further comprising periodically checking the data communication link between the remote user interface computer and the identified medical device to ensure that a communication connection is maintained.

6. The method of claim 1, wherein the selected medical device includes a blood treatment machine.

7. The method of claim 6, wherein the blood treatment machine includes a hemodialysis machine.

8. The method of claim 1, wherein the medical devices are hemodialysis devices.

9. The method of claim 8, wherein the medical devices further include one of a blood pressure monitor, a thermometer, and a weight scale.

10. The method of claim 1, wherein the verification key sequence is a random sequence of keys to be pressed by the patient on the selected medical device the patient intends to use.

11. The method of claim 1, wherein the operator and the patient are the same person.

12. The method of claim 1, further comprising periodically checking a data communication connection between the remote user interface computer and one of the connected medical devices to ensure that a communication connection is maintained.

13. The method of claim 12, further comprising periodically verifying the identification and pairing between the remote user interface computer and one of the connected medical devices.

14. The method of claim 13, wherein the periodic verification of the identification and pairing between the remote user interface computer and one of the connected medical devices is initiated automatically.

15. The method of claim 13, wherein the periodic verification of the identification and pairing between the remote user interface computer and one of the connected medical devices is initiated manually.

16. The method of claim 1, wherein the database is disposed in a server accessible over a computer network.

17. The method of claim 1, wherein the database is disposed on a computer readable medium adapted to be directly coupled to the remote user interface computer.

18. The method of claim 17, wherein the computer readable medium includes a nonvolatile memory device.

19. The method of claim 1, wherein the patient identification information includes a patient identifier code.

20. The method of claim 1, wherein the patient identification information includes a patient name.

21. The method of claim 1, wherein the list of available devices includes a list of blood treatment machines.

22. The method of claim 1, wherein the list of available devices includes a list of hemodialysis treatment machines.

* * * * *